(12) United States Patent
Bryhan et al.

(10) Patent No.: US 8,497,126 B2
(45) Date of Patent: Jul. 30, 2013

(54) METHOD OF MAKING ENHANCED CELL GROWTH SURFACE

(75) Inventors: Marie D. Bryhan, Lindley, NY (US);
Paul E. Gagnon, Jr., Wells, ME (US);
Zhong-he Shen, Grayslake, IL (US);
Oliva V. LaChance, Dover, NH (US);
Hongming Wang, Kennebunk, ME (US)

(73) Assignee: Corning Incorporated, Corning, NY (US)

( * ) Notice: Subject to any disclaimer, the term of this patent is extended or adjusted under 35 U.S.C. 154(b) by 1439 days.

(21) Appl. No.: 11/824,289

(22) Filed: Jun. 29, 2007

(65) Prior Publication Data
US 2008/0003663 A1    Jan. 3, 2008

Related U.S. Application Data

(60) Provisional application No. 60/817,814, filed on Jun. 30, 2006.

(51) Int. Cl.
*C12N 5/02*    (2006.01)
(52) U.S. Cl.
USPC .................. 435/402; 435/287.1; 264/405
(58) Field of Classification Search
USPC ................. 264/405; 435/402, 287.1
See application file for complete search history.

(56) References Cited

U.S. PATENT DOCUMENTS

| | | | | |
|---|---|---|---|---|
| 5,804,231 A | * | 9/1998 | Prophet et al. | 425/570 |
| 5,808,012 A | * | 9/1998 | Donofrio et al. | 530/356 |
| 6,164,954 A | * | 12/2000 | Mortazavi et al. | 425/549 |
| 6,617,152 B2 | | 9/2003 | Bryhan et al. | 435/283.1 |
| 2003/0180903 A1 | * | 9/2003 | Bryhan et al. | 435/180 |

OTHER PUBLICATIONS

B. W. Callen, et al. "Remote plasma and ultraviolet-ozone modification of polystyrene", Journal of Vacuum Science and Technology A 13(4), Jul./Aug. 1995, pp. 2023-2029.
Shuguang Zhang, et al. "Biological surface engineering: a simple system for cell pattern formation", Biomaterials 20 (1999) pp. 1213-1220.
R. G. Flemming, et al. "Effects of synthetic micro-and nano-structured surfaces on cell behavior", Biomaterials 20 (1999) pp. 573-588.
Bruce Banks, et al. "The Development of Surface Roughness and Implications for Cellular Attachment in Biomedical Applications", NASA/TM-2001-211288, Nov. 2001.

* cited by examiner

*Primary Examiner* — Michael Hobbs
(74) *Attorney, Agent, or Firm* — Susan S. Wilks

(57) ABSTRACT

A method of producing an improved cell growth surface and cell attachment surface. According to the present invention, a polymer article is molded at temperature in excess of 550° F. at the injection tip. After allowing the part to cool, a stream of plasma comprised of activated gaseous species generated by a microwave source is imparted on the article. This stream is directed at the surface of a polymer substrate in a controlled fashion such that the surface is imparted with attributes for cell adhesion superior to those of untreated polymer or polymer treated by other methods.

5 Claims, 2 Drawing Sheets

METHOD OF MAKING ENHANCED CELL GROWTH SURFACE

CROSS-REFERENCE TO RELATED APPLICATIONS

This application claims the benefit of U.S. Provisional Application Ser. No. 60/817,814 filed on Jun. 30, 2006 and entitled "Method of Making Enhanced Cell Growth Surface" which is incorporated by reference herein.

BACKGROUND

The present invention relates generally to the field of cell growth laboratory ware and more specifically a product that facilitates cell growth. An apparatus and method for performing the surface treatment is also provided by the present invention.

The cultivation of living cells is a key component in, among other things, the drug discovery process. Many devices are sold for purposes of cell culture including roller bottles, flasks, dishes, multiwell plates, cell harvesting units, etc. Typically these items of laboratory ware are molded from polymers having a sufficient mechanical stability and strength to create the necessary substrate surface for cell attachment and growth.

Generally, cell growth containers or substrates need to be 'surface treated' after molding in order to make the surface hydrophilic and to enhance the likelihood for effective cell attachment. Surface treatment may take the form of a surface coating, but typically involves the use of directed energy at the substrate surface with the intention of generating chemical groups on the polymer surface. These chemical groups will have a general affinity for water or otherwise exhibit sufficient polarity to permit stable adsorption to another polar group. These functional groups lead to hydrophilicity and or an increase in surface oxygen and are properties recognized to enhance cell growth. Such chemical groups include groups such as amines, amides, carbonyls, caboxylates, esters, hydroxyls, sulfhydryls and the like. Examples of directed energy include atmospheric corona discharge, radio frequency (RF) vacuum plasma treatment, and DC glow discharge. These polymer surface treatment methods have displayed varying degrees of success and their effects tend to decay over time.

In the case of plasma treatment, plasmas are created when a sufficient amount of energy is added to gaseous atoms and/or molecules, causing ionization and subsequently generating free electrons, photons, free radicals, and ionic species. The excitation energy supplied to a gas to form a cold plasma can originate from electrical discharges, direct currents, low frequencies, radio frequencies, microwaves or other forms of electromagnetic radiation. Plasma treatments are common for surface modification in the microelectonic and semiconductor industries. As mentioned, atmospheric corona and RF plasma treatment are commonly used for polymeric surface activation for cell growth substrates as well as medical implants.

Current standard practices for growing adherent cells in cell culture involves the use of defined chemical media to which is added up to 10% volume bovine or other animal serum. The added serum provides additional nutrients and/or growth promoters. In addition, serum proteins promote cell adhesion by coating the treated plastic surface with a biolayer matrix to which cells can better adhere. The addition of serum is typically required to support the normal growth of the majority of cell lines. While advantageous for cell growth, serum can have adverse effects by introducing sources of infection or abnormally inducing expression of unwanted genes exposed to serum.

An advance over the standard practices details the use of microwave plasma surface treatment. In such a process, a stream of plasma is comprised of activated gaseous species generated by a microwave source. This stream is directed at the surface of a polymer substrate in a controlled fashion such that the surface is imparted with attributes for cell adhesion far superior to that of untreated polymer or polymer treated by other methods described above. This process is more fully described in U.S. Pat. No. 6,617,152 and 2003/0180903, the contents of which are incorporated herein by reference. Surfaces for cell culture which enhance cell attachment are desired. In addition, surfaces for cell culture which enhance cell attachment without the use of animal products such as serum are desired.

SUMMARY OF THE INVENTION

According to the present invention, a polymer part is molded at high temperatures relative to standard molding techniques. After cooling, the part is then subjected to a stream of plasma comprised of activated gaseous species generated by a microwave source. This stream is directed at the surface of a polymer substrate in a controlled fashion. The surfaces treated according to the present invention exhibit superior cell growth characteristics than those achieved by currently known methods.

DETAILED DESCRIPTION

Typically, injection molded polymer articles for use as disposable cell culture vessels are molded at temperatures of between 400° F. and 500° F. However, it has been discovered that maintaining all other standard molding conditions (pressure, fill time, cycle time, etc.) but raising the molding temperatures imparts characteristics in the article surface that, after proper post treatment processing, aids in the attachment and growth of cells. Although not intending to being bound by theories of operation, it is thought that molding at higher temperature creates a surface with greater texturing than those surfaces molded at relatively lower, industry standard temperatures. To that end, it is preferable that molding occur at temperatures in excess of 500° F., 550° F., and even in excess of 600° F. For purposes of this invention, ideal molding temperatures may vary depending on the type of polymer. For polystyrene, articles should be molded at temperatures of 550-650° F., 590-630° F., or 600-620° F. Cycle times for molding will typically run 12-17 seconds. Once removed from the mold and cooled, the articles are subjected to a microwave plasma stream.

Figure 1:
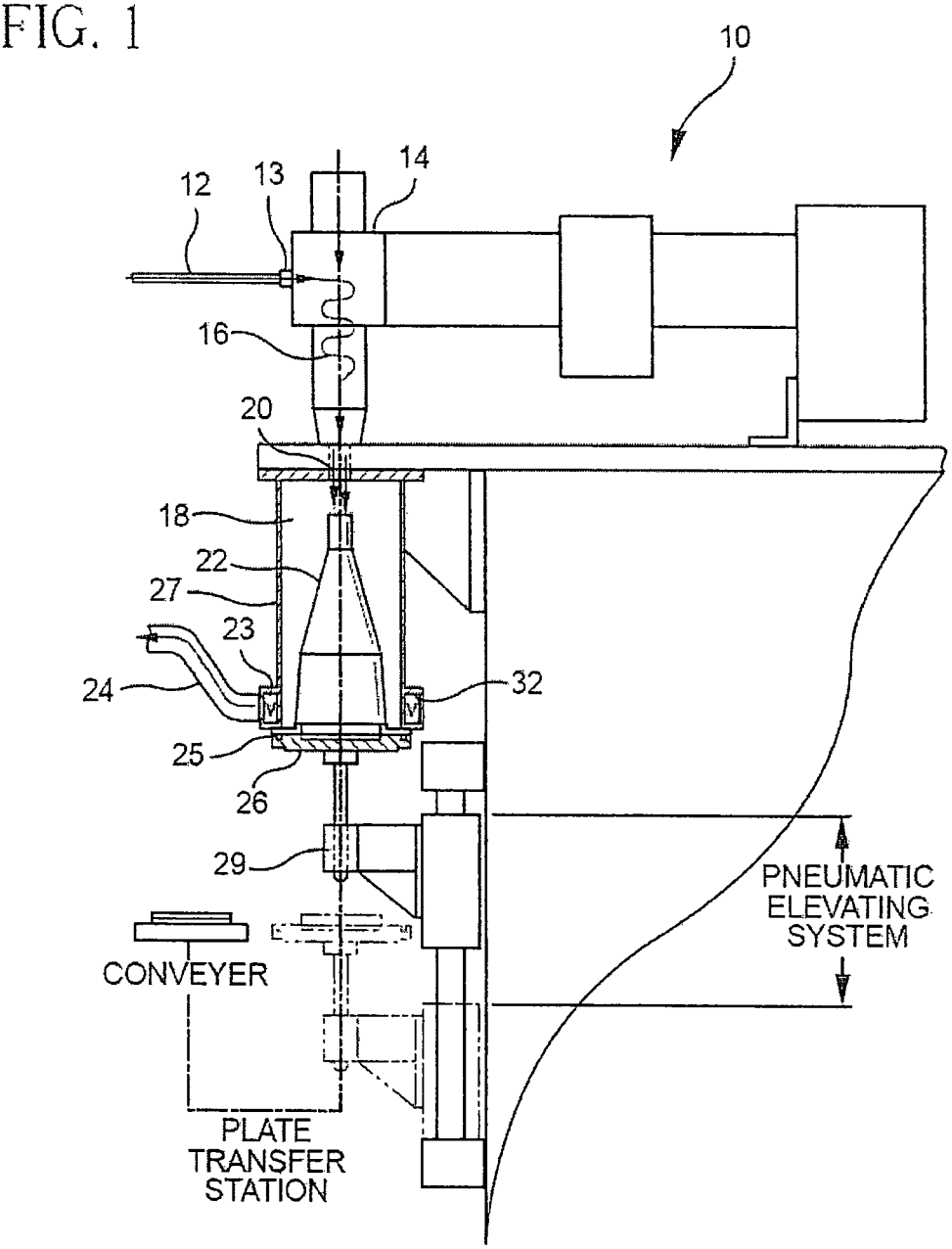
FIG. 1 is a schematic drawing of the microwave plasma treatment apparatus of the present invention.

With reference to FIG. 1, a basic construction of the microwave plasma stream apparatus for carrying out the method of the present invention is provided. A 2.45 GHz microwave generator 10 (MKS Astex, Wilmington, Mass.) serves as the energy source of this apparatus. The equipment preferably includes a generator, circulator, dummy load, tuner, and applicator. A gas line 12 connects to a gas source and delivers the process gas, which when sufficiently energized creates a continuous stream of activated or ionized gas. Suitable plasma gases include argon, nitrogen, oxygen, nitrous oxide, ammonia, carbon dioxide, helium, hydrogen, air and other gases known to those of skill in the art. A plasma chamber 14 serves as a manifold for the reaction between gas and microwave energy, and is in fluid communication with both the gas line 12, via a valve 13, as well as the microwave generator 10. A conduit 16 connects the plasma chamber with a treatment chamber 18 through an aperture 20. Within the first or outer treatment chamber 18, a second or inner treatment chamber 22 is located. The inner chamber has a frusto-conical baffle section which serves to contain the plasma flow and direct it onto a part that is placed at its base. In this embodiment, the inner chamber shares a common base 25 with the outer chamber. The approximate 1-6 inch gap between the aperture and the neck of the second treatment chamber enable the plasma to flow out of the outer treatment chamber through a valved vacuum line 24. A pneumatic elevating system 29 may be employed to move the base portion 25 away from the treatment chamber in order to remove treated parts and place new parts into the inner chamber in an automated fashion. The conduit 16 and outer treatment chamber may be made from conductive or nonconductive materials, especially quartz, aluminum or stainless steel. The inner treatment chamber may be made from a nonconductive material, and most preferably, quartz.

In operation, the apparatus of FIG. 1 performs as follows: A molded polymer part to be treated is located within the inner chamber 22. For purposes of illustration, a multiwell plate 26 has been placed on the base 25, but the inner and outer chamber may be shaped, dimensioned and configured to accommodate any of a variety of polymer parts. A vacuum seal is created between the base 25 and the sidewalls 27 of the outer chamber. To enable continuous flow, vacuum pumping is maintained through the process. The valves 13, 23 are opened and the process gas is allowed to flow into the plasma chamber 14, through the aperture 20 and into the dual chambered treatment area. The gas flows at a pressure preferably between 100 and 2,000 millitorr, and more preferably between 200 and 300 millitorr. The gas is preferably set to flow at a rate of 100 to 5,000 cc/min, and more preferably between 400 and 600 cc/min. While the process may run at any range of temperatures, it preferably runs between 40 and 150 degrees Fahrenheit and more preferably at room temperature, or approximately 72 degrees Fahrenheit. The microwave generator is engaged to create an output of between 300 and 10,000 watts, and preferably between 300 and 3,000 watts. The microwave energy entering the plasma chamber 14 interacts with the gas entering the plasma chamber resulting in activation of the gas thereby creating the resultant plasma. Due to the constant flow characteristics of the assembly, the plasma is directed through the conduit 16, through the aperture 20, and into the treatment chamber. The stream or jet created by the plasma flow through the conduit and aperture is directed into the outer treatment chamber 18, subsequently into the inner treatment chamber 22, and onto the polymer part 26 placed at the base 25 of the chamber. Flow out of both the inner chamber 22 and outer chamber 18 is assured due to the vacuum line 24, which serves to evacuate the dual chambered treatment area. It should be noted that due to the inner treatment chamber 22, the plasma stream is directed onto the part as opposed to directly toward the outlet valve 23, thereby enabling the part 26 to have optimal contact with the stream.

The inner treatment chamber 22 should be entirely enclosed and sealed from the outer chamber 18, but for the opening at the neck.

The plasma is energized for between 1 second and 5 minutes and more preferably for between 5 and 20 seconds. Once treatment is complete, the microwave energy is ceased, valves are closed, an atmospheric vent valve 32 is opened to introduce nitrogen or dry air to the system and in order to return all the chambers to atmospheric pressure. After normalization of pressure, the part is removed by operating the pneumatic elevating system 29. Optimally, a computer control system performs the steps outlined above in an automated fashion. After removal, the part is preferably given a standard sterilization treatment by exposure to gamma radiation.

The surface of the polymeric substrate to be treated can have any shape, for example it can be flat, curved or tubular. Preferably, it is a flat planar surface. For purposes of this invention, the polymeric substrate can be biodegradable or non-biodegradable. Preferably, to be useful in both in vivo and in vitro applications, the polymeric substrates of the present invention are non-toxic, biocompatible, processable, transparent for microscopic analysis, and mechanically stable.

A large variety of polymers may be used as substrates in the articles of the present invention. Examples of polymers useful in the present invention include polyacrylates, polymethylacrylates, polycarbonates, polystyrenes, polysulphones, polyhydroxy acids, polyanhydrides, polyorthoesters, polypropylenes, polyphosphazenes, polyphosphates, polyesters, nylons or mixtures thereof.

Examples of substrates that can be treated by the method disclosed herein include but are not limited to: flasks, dishes, flat plates, well plates, bottles, containers, pipettes, tubes, medical devices, filter devices, membranes, slides, and medical implants. These items are typically formed by commonly practiced techniques such as injection molding, extrusion with end capping, blow molding, injection blow molding, etc.

Although the invention is targeted for cell adhesion, attachment, and growth, the resultant polymer substrate surface promotes adsorption of a number of biologically active molecules including but not limited to: peptides, proteins, carbohydrates, nucleic acid, lipids, polysaccharides, or combinations thereof, hormones, extracellular matrix molecules, cell adhesion molecules, natural polymers, enzymes, antibodies, antigens, polynuceotides, growth factors, synthetic polymers, polylysine, drugs and other molecules.

Any cell type known to one of skill in the art may be attached and grown on the treated substrates of the present invention. Examples of cell types which can be used include nerve cells, epithelial cells, mesenchymal stem cells, fibroblast cells, and other cell types.

While the mechanism for enhanced cell attachment to the substrate treated according to the present method is not fully understood, it is believed to stem from three general characteristics: surface morphology, chemical functionalities, and surface energy.

EXAMPLE

Figure 2:
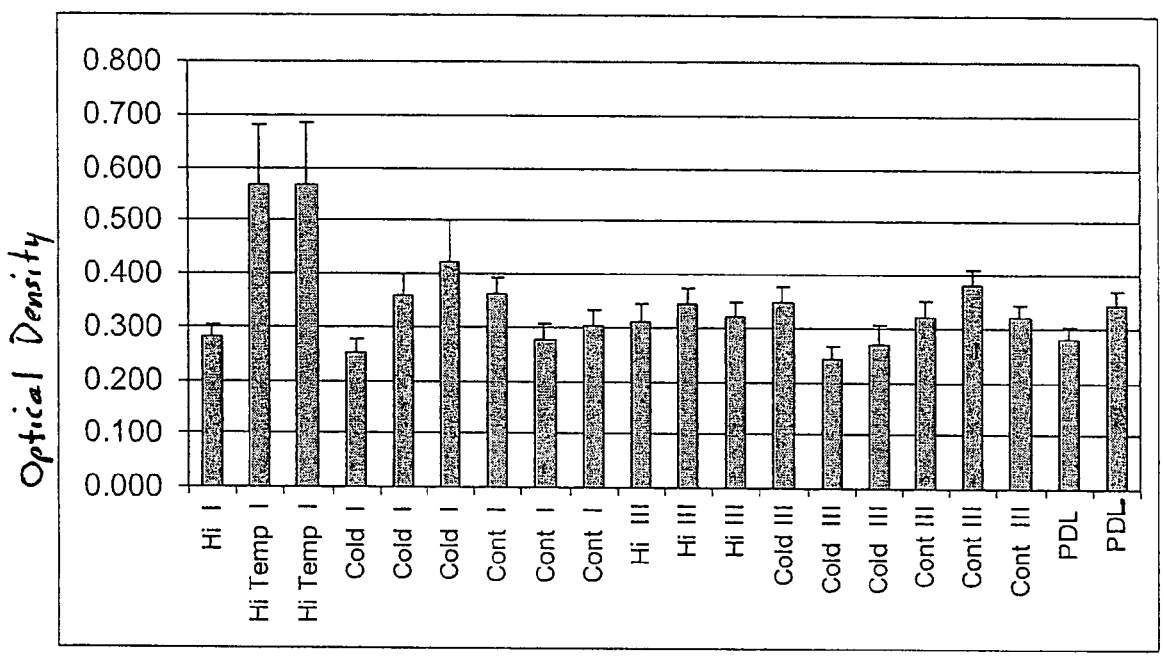
FIG. 2 is a graphical representation of a comparative cell growth study performed with injection molded polystyrene microplates molded at a variety of temperature and with 2 different plasma gases.

FIG. 2 is a graphical representation of a comparative cell growth study performed with injection molded 96-well polystyrene clear plates that have been molded at a variety of temperature conditions and subjected to two different types of microwave plasma treatments. A Cincinnati Milacron 300 ton injection molding machine was employed for making the plates that were later post treated with microwave plasma.

The molding conditions were as follows: For "High Temperature" molding, temperatures at the injection tip were approximately 610° F. For "Cold Temperature" molding, temperature at the injection tip was approximately 570° F. For the "Cont" or control condition, a more standard molding temperature of 460° F. was employed. In "Type I" treatment, the plasma gas utilized was a nitrous oxide. The nitrous oxide generally imparts a negative charge to the treated surface. In "Type II" treatment, the plasma gas utilized was ammonia. Ammonia, when utilized as the plasma gas tends to impart a negative charge to the treated surface. Finally, all samples were compared to plates treated with known chemical cell attachment coating, poly-D lysine (PDL). Cells were seeded at 70,000 cells per well of the plate and tested in triplicate. Cell growth conditions were measured by optical density readings under 10% serum growth conditions for 24 hours. Optical density assay quantification was carried out by a standard calorimetric kit (Cell Titer 96-Aq., Promega Corporation, Madison, Wis.). The cell line used was Hek-293. Cells were seeded onto all surfaces at the same time, with the same initial number of cells, under the same conditions. Table 1 displays the data.

| Molding Condition | Treatment Gas | Optical Density |
| --- | --- | --- |
| High | Nitrous Oxide (Type I) | 0.281 |
| High | Nitrous Oxide | 0.568 |
| High | Nitrous Oxide | 0.569 |
| Low | Nitrous Oxide | 0.250 |
| Low | Nitrous Oxide | 0.360 |
| Low | Nitrous Oxide | 0.421 |
| Control | Nitrous Oxide | 0.362 |
| Control | Nitrous Oxide | 0.277 |
| Control | Nitrous Oxide | 0.303 |
| High | Ammonia (Type II) | 0.312 |
| High | Ammonia | 0.345 |
| High | Ammonia | 0.321 |
| Low | Ammonia | 0.349 |
| Low | Ammonia | 0.244 |
| Low | Ammonia | 0.269 |
| Control | Ammonia | 0.320 |
| Control | Ammonia | 0.380 |
| Control | Ammonia | 0.321 |
| Poly-D Lysine | None | 0.281 |
| Poly-D Lysine | None | 0.342 |

As demonstrated in the graph of FIG. 2, the microwave nitrous oxide plasma treatment molded at high temperatures significantly outperformed the plates molded at different conditions.

From the foregoing description of the various preferred embodiments, it should be appreciated that the present invention may take many various forms and that the present invention is to be limited only by the following claims.

We claim:

1. A method for creating a polymer article having a working surface upon which cells can be cultured comprising the steps of:
   a) molding a polystyrene polymer article where the molding temperature at the injection tip is greater than 600° F., and
   b) subjecting said working surface of said article to a gaseous stream that has been energized by microwave energy.

2. The method of claim 1, wherein the working surface includes at least a portion of a flask, a dish, a flat plate, a well plate, a bottle, a container, a pipette, a tube, a medical device, a filter device, a membrane, a slide, or a medical implant.

3. The method of claim 2, wherein the working surface includes at least a portion of a flask, a roller bottle, or a multiwell plate.

4. The method of claim 1 wherein the gaseous stream is activated argon, nitrogen, oxygen, nitrous oxide, ammonia, carbon dioxide, helium or hydrogen.

5. The method of claim 4 wherein the gaseous stream is activated nitrous oxide.

* * * * *